US00PP15159P3

(12) United States Plant Patent
Clark et al.

(10) Patent No.: US PP15,159 P2
(45) Date of Patent: Sep. 21, 2004

(54) PEACH TREE—NAMED 'WHITE RIVER' CULTIVAR

(50) Latin Name: *Prunus persica*
Varietal Denomination: White River

(75) Inventors: John Reuben Clark, Fayetteville, AR (US); James Norman Moore, Fayetteville, AR (US)

(73) Assignee: University of Arkansas, Fayetteville, AR (US)

( * ) Notice: Subject to any disclaimer, the term of this patent is extended or adjusted under 35 U.S.C. 154(b) by 117 days.

(21) Appl. No.: 10/268,442

(22) Filed: Oct. 8, 2002

(65) Prior Publication Data

US 2004/0139508 P1 Jul. 15, 2004

(51) Int. Cl.[7] ..... A01H 5/00

(52) U.S. Cl. ..... Plt./196

(58) Field of Search ..... Plt./196

*Primary Examiner*—Kent Bell
*Assistant Examiner*—S. B. McCormick-Ewoldt

(57) ABSTRACT

Description and specifications of a new and distinct peach variety which originated from seed produced by a hand pollinated cross of Loring (non-patented) and NJ-257 (non-patented) is provided. This new peach variety can be distinguished by its features of late mid-season ripening, high yields of high-quality, attractive, freestone, white-flesh fruits, and good plant vigor along with good resistance to bacterial spot disease.

3 Drawing Sheets

Botanical classification: Genus/species: *Prunus persica.* Cultivar: 'White River'.

SUMMARY OF THE INVENTION

The new and distinct variety of peach originated from a hand pollinated cross of Loring (non-patented)×NJ 257 (not-patented) made in 1982 by Dr. Fred Hough, Emeritus Professor at Rutgers University, New Brunswick, N.J. Dr. Hough donated the seeds from this cross to the University of Arkansas Agricultural Experiment Station in Fall, 1982. The female parent plant used in this hybridization (Loring) is a commercial peach variety available in commerce and the male parent (NJ 257) had not been publicly released and is unavailable in commerce. The major difference in the parents is that Loring is a yellow-flesh peach and NJ 257 is white flesh. NJ 257 thus is the contributor of the genes for white flesh in 'White River'. Both the parents and the instant variety are the genus and species *Prunus persica.*

The seeds resulting from this controlled hybridization were germinated in a greenhouse in the late winter/spring of 1983 and planted in a field on the Arkansas Agricultural Experiment Station near Clarksville, Ark. The seedlings fruited during the summer of 1986 and one, designated Arkansas 376, was selected for its white flesh, late mid-season ripening, large fruits, attractive fruit appearance, good fruit quality, and resistance to bacterial spot. During 1986, the original plant selection was propagated asexually, at the above noted location, by budding onto standard peach rootstock variety 'Lovell' (non-patented) and a test plot of two plants was established. Subsequently, larger test plantings have been established with asexually multiplied plant at two additional locations in Arkansas (Clarksville and Hope, Ark.).

The new variety has been asexually multiplied several times since 1986 at this location by budding onto 'Lovell' peach rootstock and no incompatibility with peach rootstock has occurred following budding. During all asexual multiplication, the characteristics of the original plant have been maintained and no aberrant phenotypes have appeared.

Plants of the new variety are vigorous and productive, and trees are standard in size, well branched and symmetrical with an upright to semi-spreading growth habit, comparable to other peach trees (*Prunus persica*). Trees express a high level of resistance to both foliar and fruit infection of bacterial spot [*Xanthomonas campestris* pv. *pruni* (Smith) Dye]. The new variety consistently is more resistant to bacterial spot than are the standard white peach varieties 'Carolina Belle' (not patented) and 'Stark ® Summer Pearl™' (not patented). The new variety blooms in the spring 3 days later than 'Carolina Belle' and 2 days later than 'Stark ® Summer Pearl™'. No winter cold injury has been observed on wood or buds of the new variety in Arkansas tests where minimum temperatures have reached −23° C. Chilling requirement to break dormancy is estimated to be 750 hours below 7° C.

Fruit of the new variety ripens mid-late to late season, averaging 8 days after 'Carolina Belle' and 8 days before 'Stark ® Summer Pearl™' reference white peach varieties. Average ripening date is July 20 in west-central Arkansas (Clarksville). Fruit of the new variety rarely has split pits, a serious fruit disorder of some peach varieties. Fruit yields have been very good and have averaged higher than the comparison peach varieties 'Carolina Belle', 'Redhaven' (not patented), and 'Cresthaven' (not patented) in test comparisons.

The fruit is round in shape, without a prominant tip but an occasional slight bulge at the suture. Fruits are attractive with an average 68% bright red blush, and 32% white or cream skin background color. In some years the red blush was up to 80% of the fruit skin surface especially when fruits are exposed to more sunlight than those fruits growing in the shaded canopy. Fruit finish is good with no blemishes. The fruit skin has average pubescence like other peaches. The flesh of the fruit is white in color and has some red pigment in the flesh, mostly around the stone or pit. Flesh is melting in texture but is firm and retains firmness until full maturity. The fruit is a freestone, in that the flesh does not adhere to the pit. Fruit size is large averaging 246 g.

The fresh fruit rates very good in flavor, and was rated highly in evaluations. Fruits average 14.5% soluble solids. The flavor is sweet and mildly subacid, with a distinct white peach aroma.

The distinctive features of the new variety are its late mid-season ripening, high yields of high-quality, attractive, freestone, white-flesh fruits, and good plant vigor along with good resistance to bacterial spot disease.

The new variety has been named the 'White River' cultivar.

BRIEF DESCRIPTION OF THE PHOTOGRAPHS

The accompanying photographs show typical specimens of the fruit (FIGS. 1 and 2) and leaf (FIG. 3) of the new variety in color as nearly true as it is reasonably possible to make in a color illustration of this character.

DETAILED BOTANICAL DESCRIPTION OF THE NEW VARIETY

The following is a detailed description of the botanical and pomological characteristics of the subject peach. Color data are presented in Royal Horticultural Society Colour Chart designations and are supplemented with readings from a Minolta Chroma Meter CR-200, version 3.0, which measures absolute chromaticity in tristimulus values L, a, and b. Calibration was performed using a standard white plate supplied by the manufacturer.

Where dimensions, sizes, colors and other characteristics are given, it is to be understood that such characteristics are approximations of averages set forth as accurately as practical.

The descriptions reported herein are from specimens grown at Clarksville, Ark. (except as noted) and are from trees grown in trickle (drip) irrigated orchards growing on a Linker fine sandy loam soil. The data were collected from eight-year old trees of the instant variety except yield data that were taken on five-year-old trees (except as noted) in a replicated test planting.

Plant:

*Size.*—Mature trees (5 years of age and older) average 3.2 m to 3.5 m in height and 4.7 to 5.8 m in spread or width, and a semi-upright growth habit, as grown on 'Lovell' rootstock using an open-center training system commonly used on peaches. Tree size is comparable to that of the 'Carolina Belle' and 'Stark ® Summer Pearl™' varieties.

*Growth.*—Vigorous, symmetrical form, good canopy development. Vigor comparable to that of the 'Carolina Belle' and 'Stark® Summer Pearl™' varieties.

*Productivity.*—Very productive and consistent from year to year. Yield measured 49.5 kg/tree on five-year old trees and exceeding that of 'Carolina Belle' with 33.9 kg/tree in a test planting of identical age and growing conditions. In a six-year-old planting at Hope, Ark., 'White River' yielded 92.1 kg/tree, exceeding that of 'Cresthaven' with yield of 58.0 kg/tree and 'Redhaven' of 31.7 kg/tree.

*Cold hardiness.*—Wood and dormant buds hardy to −23° C.

*Disease resistance.*—Leaves and fruit near fully resistant to bacterial spot under growing conditions where bacterial spot infection is often very severe on susceptible genotypes. No bactericides were used in the development or evaluation of the instant cultivar. Evidence of bacterial spot infection was less than that of 'Carolina Belle' in all years of evaluation. A commercial fungicide program was utilized in orchards used in the development and evaluation of the instant variety, thus no resistant to brown rot or scab, the other common diseases at Clarksville, Ark., was determined.

*Insect resistance.*—Insecticides were applied to orchards used in the development of the instant variety to control the common insects at the location including oriental fruit moth, plum curculio, stinkbug, tarnished plant bug, lesser peach tree borer, and greater peach tree borer. Therefore no insect resistance was determined in the testing of the instant variety.

Foliage/shoots/branches:

*Shoots.*—Glabrous. Current growing-season mature shoot length 67.6 cm; diameter base 0.63 cm, midpoint 0.41 cm, terminal 0.24 cm. Current growing-season mature shoot color: abaxial — Yellow-Green Group (144C); adaxial — Greyed-Orange Group (176A). (measured in July of the growing season). Dormant-season shoot (branch): length 86.9 cm; diameter at base 0.93 cm; diameter at midpoint 0.61 cm; diameter at terminal 0.33 cm. Dormant-season shoot color Greyed-Purple Group (183A); Dormant-season shoot texture smooth.

*Leaves.*—Simple, alternate, glabrous, lanceolote, petiolate, deciduous. Venation pinnate; base acute; terminal or apex acuminate; margin serrated. Mature leaf size: length 18.1 cm; width midpoint 4.5 cm. Leaf serrations; 5.2/cm. Mature leaf color: abaxial — Yellow-Green Group (147B), L=51.65, a=9.50, b=15.21; adaxial — Yellow-Green Group (147A), L=47.75, a=−7.35, b=10.90; and anthocyanin not present on abaxial or adaxial side of mature leaves on midrib or other location. Young leaf color: abaxial — Yellow-Green Group (146C), L=54.86,a=−16.62, b=30.18; adaxial — Yellow-Green Group (144a), L=48.12; a=−19.10, b=30.75; anthocyanin not present on abaxial or adaxial side of young leaves on midrib or other location. Petiole length — mature leaf: 0.79 cm. Leaf glands: reniform, 2 per leaf usually, located on basal portion of leaf blade near juncture with petiole. Leaf glands are 0.87 cm in width and 0.80 cm in length and color of glands is Greyed-Orange Group (176B).

*Buds.*—Flower buds ovoid in shape; size at the termination of the growing season 4 mm long and 3 mm wide. Number of leaf buds per 15 cm: 7, evenly distributed along the shoot. Number of flower buds per 0–15 cm from terminal: 5. Number of flower buds 15–30 cm from terminal: 9. Number of flower buds 30–45 cm from terminal: 8. Mature shoot internode length: base 1.67 cm, midpoint 2.05 cm, terminal 1.34 cm.

Bark (of mature trunk of tree):

*Color.*—Grey Green Group (197D).

*Texture.*—Rough.

Trunk (of tree 15 years of age):

*Diameter.*—21.1 cm (at 25 cm above ground level).

Flowers: Bloom occurs prior to vegetative bud break; solitary to occasional double individual flower at a single node; perfect; self-fertile.

*Date of bloom.*—First, Julian 76 (March 16); Full, Julian 82 (March 22).

*Size.*—Diameter fully open 2.90 cm.

*Type.*—Showy.

*Color.*—Red Purple Group (65D), L=76.59, a=18.62, b=0.53.

*Petals per flower.*—5.

*Length of pistil.*—0.88 cm.

*Stamens.*—Average 44/flower with pollen present, fertile and abundant.

Fruit:

*Size.*—Large, avg. 246.3 g; diameter stem end 7.43 cm, equator 7.78 cm, blossom end 7.29 cm; length base to apex 7.64 cm.

*Shape.*—Round, symmetrical, and occasionally some fruits slightly ovoid. Fruits are without pronounced tip but occasional slight suture bulge.

*Skin.*—Pubescent (fuzzy), attractive; ground color Yellow-Orange Group (20D), L=65.72, a=20.93, b=20.30, with red blush (Red Group 53B), L=46.43, a=27.97, b=14.48 over 68% of surface on average.

*Flesh.*—Yellow-White Group (158B), L=73.79, a=–0.66, b=14.15; freestone; melting texture; good firmness. Firmness when measured by a fruit pressure tester (using a McCormick model FT327 fruit pressure tester, 11 mm diameter probe, McCormick Fruit Tree Co., Yakima, Wash.) on unpeeled fruit had average firmness value of 3.6 kg. Good eating quality; flavor sweet, subacid, with pronounced white peach flavor and aroma.

*Pedicel length.*—0.70 cm.

*Pedicel diameter.*—0.34 cm.

*Pedicel color.*—Yellow-Green Group (144C).

*Ripe date.*—July 20 (Julian 202) in west-central Arkansas. Ripening of individual fruit is uniform.

*Tendency of pit to split.*—No split pits most years.

*Soluble solids.*—14.5%.

*Fruit juice pH.*—3.7.

Pit/stone:

*Size.*—Length 4.21 cm; diameter (midpoint) 2.75 cm.

*Shape.*—Slightly oblong with deep furrowing and pitting.

*Color.*—Greyed Orange Group (174A), L=39.31, a=9.13, b=12.97.

Kernel:

*Size.*—Length 1.94 cm; width 12.3 cm; diameter varies with dryness of the kernel but is up to 1.3 cm.

*Shape.*—Elliptical with a straight or slightly curved apiculate apex.

*Color.*—Greyed Orange Group (165B); L=54.98; a=15.15; b=30.78.

Uses: Fresh consumption, not evaluated for drying or other uses.

The variety: The most distinctive features of the variety are its late mid-season ripening, high yields of high-quality, attractive, freestone, white-flesh fruits, and good plant vigor along with good resistance to bacterial spot disease.

We claim:

1. A new and distinct variety of peach tree (*Prunus persica* cultivar 'White River') as herein described as illustrated, the cultivar is substantially as illustrated and described, characterized by its late mid-season reopening, high yields of high-quality, attractive, freestone, white-flesh fruits, and good plant vigor along with good resistance to bacterial spot disease.

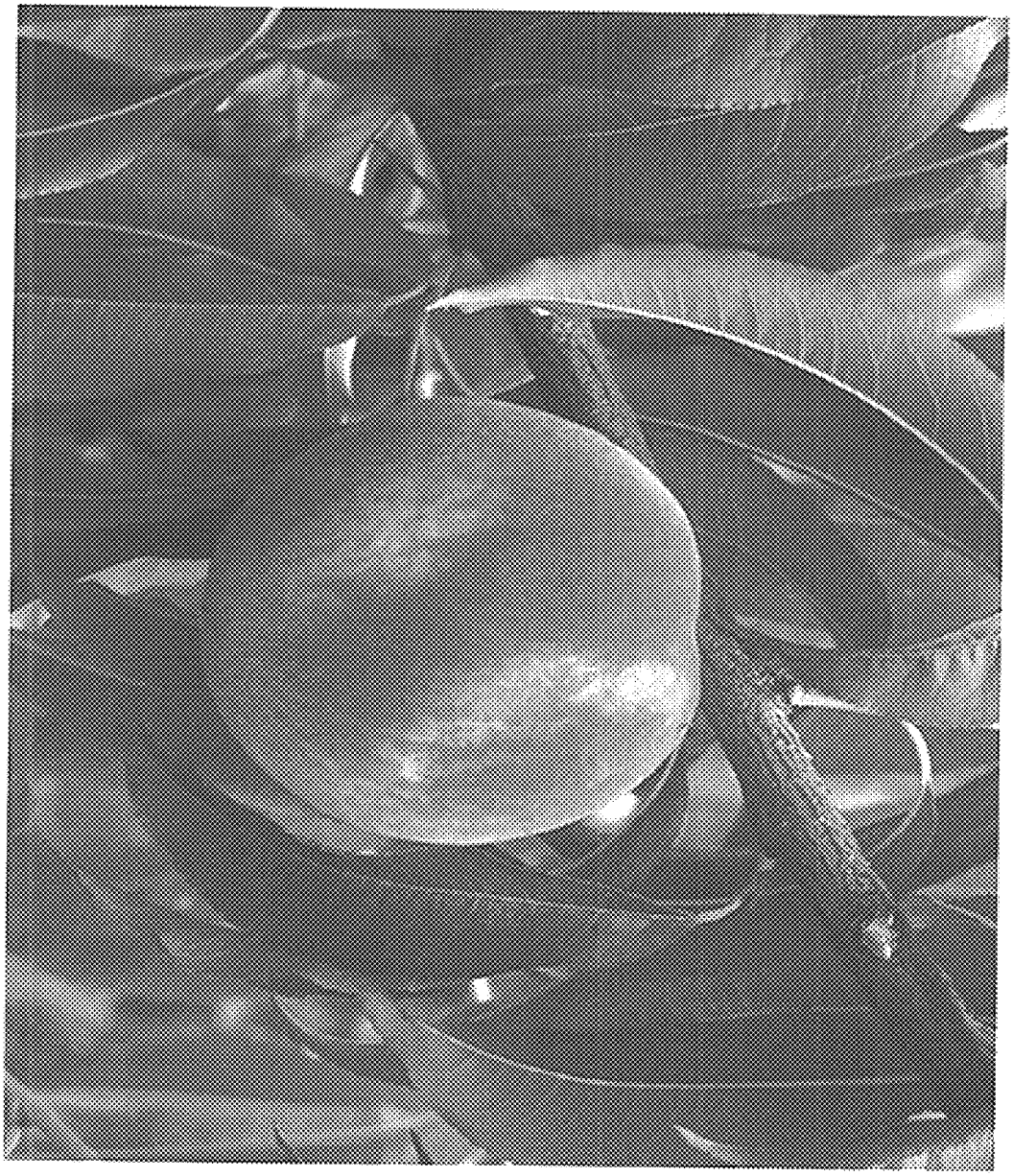

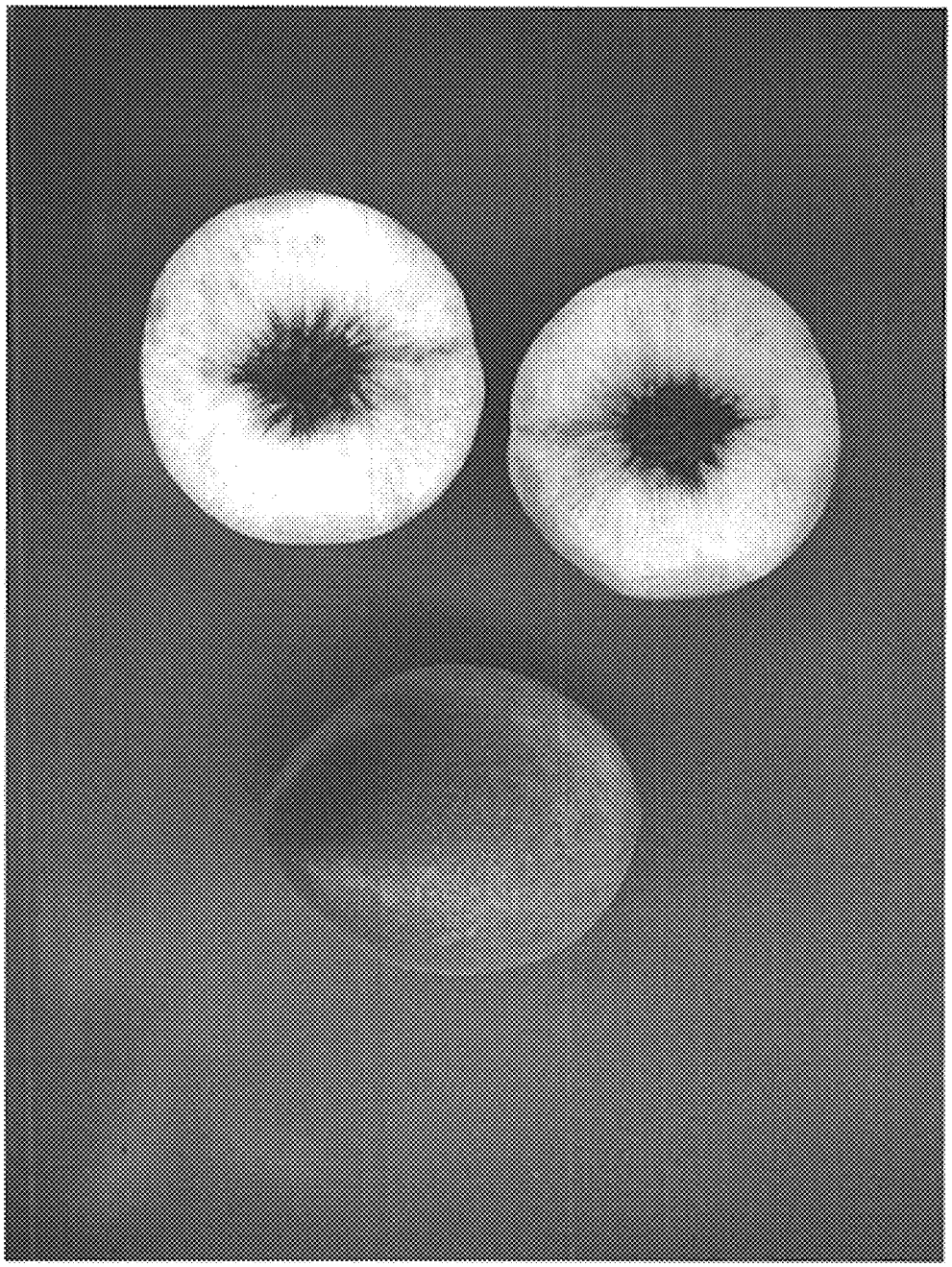

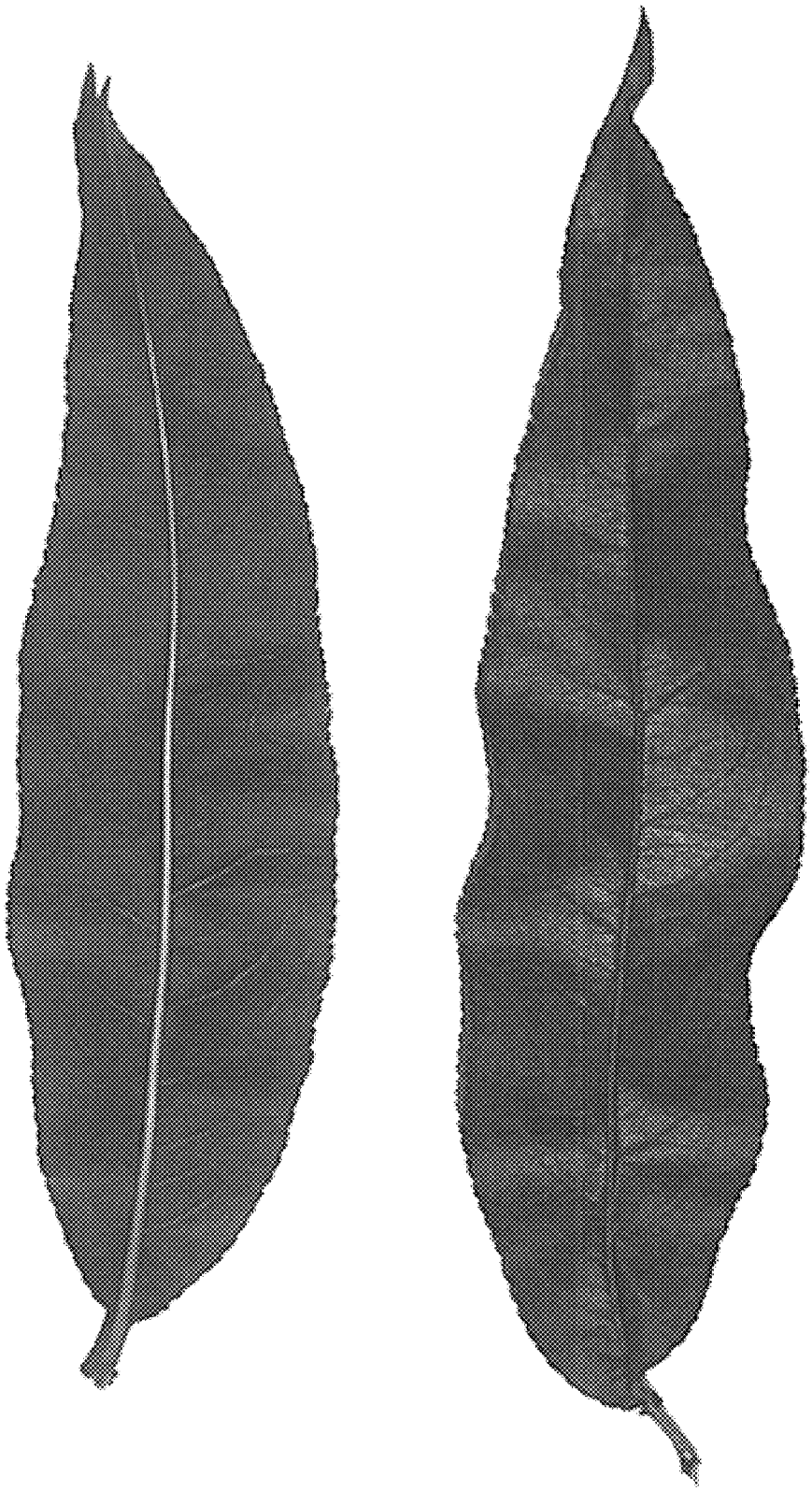

* * * * *